(12) United States Patent
Blandy

(10) Patent No.: US 8,758,472 B2
(45) Date of Patent: Jun. 24, 2014

(54) METHOD AND INTEGRATED SYSTEM FOR PRODUCING ELECTRIC POWER AND FERTILIZER

(75) Inventor: Charles William Douglas Blandy, Victoria (AU)

(73) Assignee: Industrial Ecosystems Pty Ltd, Melbourne, Victoria (AU)

(*) Notice: Subject to any disclaimer, the term of this patent is extended or adjusted under 35 U.S.C. 154(b) by 307 days.

(21) Appl. No.: 13/376,216

(22) PCT Filed: Jun. 7, 2010

(86) PCT No.: PCT/AU2010/000702
§ 371 (c)(1),
(2), (4) Date: Feb. 3, 2012

(87) PCT Pub. No.: WO2010/139028
PCT Pub. Date: Dec. 9, 2010

(65) Prior Publication Data
US 2012/0125062 A1     May 24, 2012

(30) Foreign Application Priority Data

Jun. 5, 2009  (AU) ................................ 2009902601

(51) Int. Cl.
| A62D 3/02 | (2007.01) |
| C12M 1/00 | (2006.01) |
| C05F 11/08 | (2006.01) |
| C05F 17/00 | (2006.01) |
| C05F 17/02 | (2006.01) |

(52) U.S. Cl.
USPC .................. 71/8; 71/9; 71/10; 71/28; 71/30; 71/31; 71/33; 71/34; 71/35; 435/262.5; 435/290.1

(58) Field of Classification Search
USPC ...................... 71/8–10, 28, 30, 31, 33, 34, 35; 435/262.5, 290.1
See application file for complete search history.

(56) References Cited

U.S. PATENT DOCUMENTS

| 3,965,362 A | | 6/1976 | Harvey | |
| 4,135,908 A | * | 1/1979 | Widmer | 71/9 |
| 4,184,269 A | * | 1/1980 | Kneer | 34/168 |
| 4,211,545 A | * | 7/1980 | Graefe | 71/9 |
| 4,848,026 A | * | 7/1989 | Dunn-Coleman et al. | 47/1.1 |
| 4,909,825 A | * | 3/1990 | Eigner | 71/9 |
| 5,181,950 A | * | 1/1993 | Kneer | 71/9 |
| 5,215,921 A | * | 6/1993 | Finn | 435/290.3 |
| 5,411,567 A | * | 5/1995 | Ueotani et al. | 71/9 |
| 6,340,581 B1 | * | 1/2002 | Gaddy | 435/140 |
| 6,447,437 B1 | | 9/2002 | Lee et al. | |
| 7,582,467 B2 | * | 9/2009 | Jarventie | 435/267 |

(Continued)

FOREIGN PATENT DOCUMENTS

| CN | 101407326 | 4/2009 |
| GB | 1 602 300 | 11/1981 |

(Continued)

Primary Examiner — Wayne Langel
(74) Attorney, Agent, or Firm — Clark & Brody

(57) ABSTRACT

The present invention relates to a method and system for producing electric power and fertiliser. The method comprises the steps of:
(a) combusting biomass to produce energy for the generation of electric power and an exhaust gas;
(b) producing a liquor from compounds extracted from the exhaust gas; and
(c) producing a fertiliser by composting organic materials in the presence of the liquor.

30 Claims, 1 Drawing Sheet

(56) References Cited

U.S. PATENT DOCUMENTS

| | | |
|---|---|---|
| 2008/0040975 A1 | 2/2008 | Calderon |
| 2008/0041284 A1 | 2/2008 | Calderon |
| 2010/0003741 A1* | 1/2010 | Fromson .................... 435/262.5 |
| 2010/0105127 A1* | 4/2010 | Ginsburg ...................... 435/262 |
| 2010/0107711 A1* | 5/2010 | Sinclair .............................. 71/9 |
| 2010/0199734 A1* | 8/2010 | Bottcher et al. .................... 71/8 |

FOREIGN PATENT DOCUMENTS

| | | |
|---|---|---|
| WO | 00/12448 | 3/2000 |
| WO | 2005/005786 | 1/2005 |
| WO | 2006/130965 | 12/2006 |
| WO | 2007/131301 | 11/2007 |

* cited by examiner

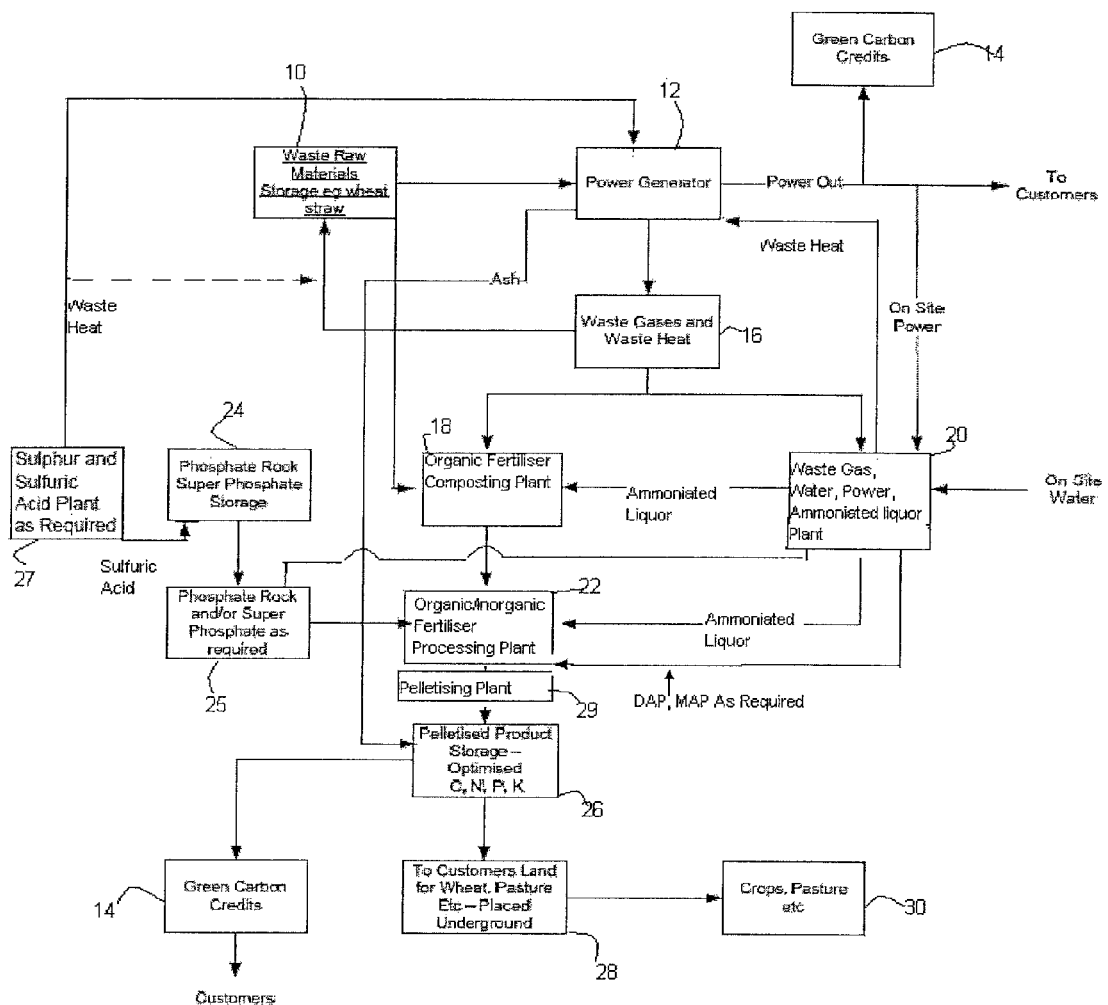

METHOD AND INTEGRATED SYSTEM FOR PRODUCING ELECTRIC POWER AND FERTILIZER

FIELD OF THE INVENTION

The present invention relates to a method and integrated system for producing electric power and fertiliser. More particularly the present invention relates to a method and integrated system for producing electric power from biomass combustion and fertiliser comprising organic and inorganic constituents.

BACKGROUND OF THE INVENTION

In this specification, where a document, act or item of knowledge is referred to or discussed, this reference or discussion is not an admission that the document, act or item of knowledge or any combination thereof was at the priority date:
(i) part of common general knowledge; or
(ii) known to be relevant to an attempt to solve any problem with which this specification is concerned.

Applicant's published International Patent Application WO 2007131301 describes an integrated system of power generation and organic fertiliser production. Co-generated waste heat from biomass combustion is beneficially re-deployed to facilitate composting of organic materials over a twelve month production cycle.

It would be advantageous to adapt the process described in WO 2007131301 to enable high-carbon, fibrous products, such as wheat straw, to be used as all or part of the raw material in the production of organic fertiliser. It would also be advantageous to minimise or even eliminate the need to separately source inorganic fertiliser components such as oxygen DAP, MAP, ammoniated superphosphate, ammonium carbamate and possibly urea for use in the process.

Published United States Patent Application No. 2002/0010382 describes a process for incinerating combustible material, such as municipal waste and/or biomass. The effluent stream resulting from the combustion of the material is sorbed of its environmentally-hazardous components in a sorbent bed prior to venting the substantially pollutant-free stream to the atmosphere. The sorbent bed is also reactivated with a reactivating agent such as carbon dioxide or air, with the pollutant-carrying reactivating agent being recycled to the combustion chamber to be decomposed by combustion.

Published International Patent Application No. WO 2005/005786 describes a process for generating electricity and producing fertiliser. The process involves incinerating a biomass material to create electricity and producing nitric acid from nitrogenous compounds extracted from exhaust gases produced during biomass combustion. Nitrogen-based fertilisers such as ammonium nitrate and calcium nitrate are produced by reacting the nitric acid with a suitable fertiliser base such as aqueous ammonia and calcium carbonate respectively.

Published United States Patent Application No. 2008/0041284 describes a method for co-producing electric power and urea from a carbonaceous material such as coal, lignite, peat or biomass The carbonaceous material is pyrolised to produce a raw rich gas and a char product. The char product is then gasified with air to produce a raw lean gas which is in turn combusted with air to generate electric power. The rich gas produced from the gasification of air is cleaned to produce carbon monoxide and hydrogen. Finally, the hydrogen is synthesized with nitrogen and carbon dioxide captured from exhaust gas of the lean gas combustion to produce urea and water.

Published United States Patent Application No. 2008/0040975 describes a process for maximising the value of a carbonaceous material such as bituminous coal, lignite, peat, coke or biomass. The process involves pyrolising the carbonaceous material to produce a first gas and a hot char. The hot char is divided into two streams, the first being directed to a gasifier to be gasified to produce a second gas. The second char stream is further divided into two sub-streams, with the first being heated to create a sub-stream of hot activated carbon. Urea is produced by combining the hot activated carbon with flue gases produced from combustion of the second gas. Finally, the urea is combined with the second activated carbon sub-stream to produce an enhanced urea fertiliser.

SUMMARY OF THE INVENTION

According to a first aspect of the present invention there is provided a method for producing electric power and fertiliser, comprising the steps of:
combusting biomass to produce energy for the generation of electric power and an exhaust gas;
producing a liquor from compounds extracted from the exhaust gas; and
producing a fertiliser by composting organic materials in the presence of the liquor.

According to a second aspect of the present invention there is provided an integrated system for producing electric power and fertiliser, the system comprising:
a biomass combustion facility for combusting biomass to produce energy for electric power and an exhaust gas; and
a composting facility for producing compost from organic materials,
wherein a liquor is produced from compounds extracted from the exhaust gas and directed into the composting facility to produce a fertiliser by composting organic materials in the presence of the liquor.

Embodiments of the present invention provide a method and integrated system in which fertiliser-related gases are stripped from the exhaust gases of biomass combustion and used in the production of a liquor, which is in turn beneficially redeployed in the production of fertiliser in a composting facility. In contrast to the power and fertiliser-generation facilities discussed above, the present invention involves recycling exhaust gases to assist in the production of an organic fertiliser at a composting facility.

The liquor assists in composting the organic materials into high-quality 'humic' compost, and also contributes inorganic fertiliser components to produce a high quality fertiliser comprising both organic and inorganic constituents. Moreover, rather than separately sourcing inorganic fertiliser components, such as from natural gas, the present invention provides an integrated, self-sufficient process, having biomass as the sole input and electrical power and organic/inorganic fertiliser as the outputs.

The ability to make a nitrogen-rich liquor from the exhaust gases allows organic raw materials with low levels of nitrogen to be composted more easily and flexibly than would otherwise be the case.

The introduction of the liquor aids the composting process and enables the production of fertilisers from a wider range of organic materials than is currently thought practicable. In particular, the introduction of the liquor enables the straw of cereal grains, such as wheat, to be efficiently composted and the carbon content to be transformed into a fertiliser.

Such a fertiliser may be optimised for the soil to which it is applied and to the particular crop to be grown. For example, the liquor may contain urea, ammonia ammonium carbamate and water. As known to those skilled in the art, urea contains approximately 47% nitrogen and ammonia 82% nitrogen. A suitable liquor can be made from 32.5% urea, 28.9% ammonia, 18.1% ammonium carbamate and 20.5% water. The liquor can be mixed with the carbon in wheat straw or other nitrogen-lacking biomass to facilitate efficient composting.

A ratio of approximately 30:1 carbon to nitrogen by weight is in a preferred embodiment recommended to start an efficient composting process in the case of wheat straw.

The ability to compost significant quantities of high lignin-biomass may also produce higher quantities of humus than are found in composts made from more readily compostable materials such as green waste.

The key organic component of the fertiliser produced by practising the method according to the invention is humus (humic acid). As known to those skilled in the art, humus is the key carbon-containing nutrient desired by plants to assist in their growth. The higher the quantity of humic acid the more efficiently plants can digest carbon nutrients. Another advantage of preferred embodiments of the invention is that the improved conversion of organic material via humic composting results in an organic fertiliser with more humus that requires less inorganic components, such as phosphorous. In fact, it appears that only about 25% to about 50% of the usual amount of phosphorous in DAP and MAP fertiliser is required when combined with high quality humus compost produced according to the invention.

The presence of the liquor in the compost also provides an efficient carbon-to-nitrogen ratio for optimal composting over long composting periods so as to optimise the production of humic acid in the compost. However, the use of in-vessel composting will have the ability to shorten and also to improve compost process control in the early stages of the process.

Systems and methods according to preferred embodiments of the present invention have the additional benefit of reducing the net volume of atmospheric carbon dioxide, in that part of the carbon dioxide removed from the atmosphere by the growing biomass is not re-introduced into the atmosphere by biomass combustion, but instead is used in the production of a liquor, which is deployed in the manner described above and eventually buried in soil.

Other economic benefits arise from the negative carbon dioxide nature of the present invention through the awarding of tradeable carbon credits. The production of electrical power from biomass also attracts carbon credits and does not increase the level of carbon dioxide in the atmosphere when using carbonated materials such as wheat straw, green garden waste, manure and recycled compost which have an annual growing cycle of less than one year.

Preferably, the system includes an inorganic fertiliser production facility, wherein the liquor is directed to both the composting facility and the inorganic fertiliser production facility.

Typically, the liquor includes one or more of ammonia, ammonium carbamate, urea and water.

Optimally, each of the ammonia, ammonium carbamate and urea are at least partially produced from nitrogenous compounds extracted from the exhaust gas. As discussed below, the hydrogen component of the ammonia, ammonium carbamate and/or urea can be suitably produced from the electrolysis of water.

In addition, each of the ammonia, ammonium carbamate and urea may be produced from nitrogenous compounds and carbon dioxide extracted from the exhaust gas.

Waste gas from biomass power generation contains in the region of 10-20% carbon dioxide as against less than 1% in ordinary air. Hence, access to such carbon dioxide is highly desirable in making ammonium carbamate and urea. Such waste gases also contain large amounts of nitrogen and some oxygen, which are also desirable as gases in their own right or as feed gases for the production of other components.

According to one embodiment, urea is produced from nitrogenous compounds extracted from the exhaust gas by:
    obtaining carbon dioxide and nitrogen from the exhaust gas;
    obtaining a source of hydrogen; and
    producing urea from the carbon dioxide, nitrogen and hydrogen.

Optionally, the hydrogen may be sourced from utilising the electric power to electrolyse water and thereby generate hydrogen.

Efficiency gains are realised from supplying the necessary hydrogen from water-electrolysis driven by electric power from the negative carbon generation energy source of the present invention.

Optionally, char may be created at the biomass production facility by pyrolysis of the biomass and reacted with water to make carbon monoxide and hydrogen. Still further, the carbon monoxide may be reacted with more water to make carbon dioxide and more hydrogen. In this way water gas can be used as a supplementary source of carbon dioxide and hydrogen.

Preferably, inorganic fertiliser components are produced from ammonia, the ammoniated liquor and phosphorus products (preferably triple superphosphate) to make ammoniated phosphates, DAP and/or MAP and then combined with the humic compost to produce a fertiliser comprising both organic and inorganic constituents.

According to this embodiment, the inorganic fertiliser components are produced in powdered form to enable convenient production of a pelletised fertiliser.

According to a third aspect of the present invention there is provided a fertiliser produced by the method according to a first aspect of the present invention or by the system according to a second aspect of the present invention.

BRIEF DESCRIPTION OF THE DRAWINGS

The invention will now be further explained and illustrated by reference to the accompanying drawing, in which FIG. 1 is a block diagram schematically illustrating the process steps and components of an embodiment of the present invention.

DETAILED DESCRIPTION OF THE DRAWINGS

Turning to FIG. 1, a method for the integrated production of electrical power and a high-quality fertiliser comprising inorganic constituents and organic nutrients is illustrated.

Waste organic material 10 such as wheat straw is collected, dried and stored. Part of the organic material is combusted to generate electrical power at a power generator 12. In turn, most of, or all, the generated power is sold to consumers.

As biomass combustion can be considered substantially carbon-neutral (i.e. carbon in equals carbon out and hence no net carbon is introduced into the atmosphere), the power generator is entitled to green carbon credits 14 under an applicable carbon trading regime Waste heat and waste gases 16 (i.e exhaust gases) are produced as a by-product of biomass combustion. As described in Applicant's International Patent Application WO 2007131301 (the contents of which are hereby incorporated by reference) waste heat 16 is redirected to a fertiliser composting plant 18 to assist in the production of a pelletised fertiliser product comprising inorganic constituents and organic nutrients.

A liquor containing ammonia, ammonium carbamate, urea and water is produced from the exhaust gas in the manner described below and supplied to the composting plant 18 in a liquid form, or to a separate production facility 22 in a crystalline form. A fertiliser product comprising organic nutrients and phosphate rock is manufactured at production facility 22 by composting organic materials in the presence of the liquor.

A separate source of phosphate rock, superphosphate and/or double or triple superphosphate is stored at facility 24 and provided to production facility 22 for use in the production of the fertiliser product.

The ammoniation is done simply by spraying a measured weight or volume of ammoniation solution into a weighted quantity of solid material and mixing in a one or two tonne rotary batch mixer. As discharged from the mixer the mixture is warm and feels moist. Upon cooking it becomes dry and friable Ammoniated products cure rapidly and are easy to handle.

The fertiliser product is pelletised at a pelletising plant 26 and sold to customers 28, who in turn utilise the fertiliser in pastures 30 as required.

It is essential to have maximum processing flexibility in composting high-carbon raw materials like wheat straw and wood waste. These have natural carbon to nitrogen ratios in the approximately 60-100:1 range (as against a 30:1 or less range essential for starting the composting process). Wheat straw and wood waste are therefore very difficult to compost without access to a significant additional source of nitrogen such as urea.

It is also desirable to produce a long-term composted, pelletised organic fertiliser product having the highest practical amount of composted carbon, which accordingly contains significant amounts of humic acid per tonne. This is because humic acid from long term composting has much higher positive plant growth impact and greenhouse abatement impact compared to a short term composted product with only small amounts of humus (humic acid). For example, wheat straw has a carbon content of about 47% by weight (dry basis) versus green garden waste with a carbon content in the approximately 15-25% carbon range (dry basis).

EXAMPLES

Examples of the approximate C:N ratio (dry basis) of various materials are shown below.

| Product | C:N Ratio |
| --- | --- |
| Cow manure | 10-15 (fresh):1 |
| Vegetable waste | 15:1 |
| Grass clippings | 20:1 |
| Tree leaves | 50:1 |
| Straw | 80:1 |
| Wood/Paper | 100+:1 |
| Micro-organisms in soils (similar to humans and animals like cattle) | 4-9:1 |

Another critical compost processing criteria is an 'aerobic' environment. A typical compost that smells signifies a lack of air (i.e. an anaerobic process). This also signifies a slowing down of the composting process, as the smell is due to nitrogen-gas compounds escaping and a corresponding rise in the C:N ratio. Hence the speed of composting and the quality of composted product is adversely affected if there is insufficient air. Moreover, having the ability to process more fibrous and hollow green waste products like wheat straw and wood waste is desirable because their structure can keep more air circulating through the compost processing heaps.

According to the present invention the process described in WO 2007131301 is modified to include a predictable on-site source of nitrogen in the form of urea. This enables the composting plant 18 to maximise the amount of humic acid via the composting process. As noted above, humic acid has a critical impact in helping plants to grow.

Organic-inorganic fertiliser pelletising plant 22 requires flexibility to produce optimum combinations of 'C' (humic acid in particular), plus 'N', 'P' and 'K'. With sufficient 'C' (humic acid), the amount of 'P' can be reduced. Also, superphosphate, double or triple superphosphate, or rock phosphate 'P' can be used (zero to low $CO_2$ waste impact). A long term composting process (3-12 months) is necessary when seeking to process high fibrous materials such as wheat straw, although in-vessel composting and maturation tends to take a shorter time. In either case, time is needed to break down the fibres so that the compost can be easily pelletised, and as stated above, to maximise humic acid and reduce the amount of 'P' required for plant growth by anything from 50% to up to 75% as shown in Applicant's greenhouse and field trial experiments.

A further factor is the ideal pH for growing plants, which is in the 6-7 range, although plants can handle a somewhat higher pH range (8-8.5) if necessary.

Another factor relates to the micro-organisms that effect the composting process—such micro-organisms need a processing water content of about 50-60% with a temperature of up to 70° C. (thermophilic bacteria). This is the temperature which destroys most weeds in high-temperature, long-term composting. The ability to maintain an approximately 70° C. temperature in winter is an existing feature of the process described in WO 2007131301.

The element 'K' also has a beneficial impact on growing plants. It should further be noted that the Applicant's green power generation process by burning wheat straw or wood wastes for electrical power creates a residual ash product which is rich in calcium (Ca) and potassium(K). This can be added to the organic-inorganic fertilizer finished product 26.

A long term composting process significantly increases the ability of the humic acid-rich composted product to absorb water. For example, 100 lbs of long term-humus compost can absorb up to twice its weight of water. This capability helps protect the growing environment of plants during periods of low rainfall and drought.

The liquor containing ammonia, ammonium carbamate, urea and water from waste gases, water and green power generated by the power generator 12 provides a predictable 'N' source (own manufacture on same site) to assist in the long term composting of raw materials such as wheat straw which has a C:N ratio of 80:1 but needs the new source of 'N' to establish the required C:N ratio of 30:1 necessary to start and maintain the composting process using a raw material like wheat straw.

According to the present invention, ammoniated liquor is used in composting, and ammoniated urea liquor is used in adding additional 'N' to the final composted fertiliser product. If available, wheat straw can be mixed with other raw materials such as green waste, cattle/pig manure, abattoir waste, waste food and existing composted product.

In addition, the composting process aims to target the optimum amount of humic carbon in the finished product at approximately 26% (i.e up to 40% on a dry basis) or higher and preferably approximately 30-39% on a dry basis). This is harder to achieve without the use of materials like straw for composting.

Producing Liquor from Power Station Exhaust Gases

As known to those skilled in the art, urea, ammonium carbamate and ammonia require the following basic elements in their manufacture:
carbon dioxide;
nitrogen; and
hydrogen.

According to the present invention, the carbon dioxide, some oxygen, possibly some nitrous oxide, and nitrogen components are obtained from exhaust gases produced during biomass combustion in the biomass-fired power generator 12.

The hydrogen component is obtained from the electrolysis of water also conducted at the biomass-fired power generator 12, as described below. Any oxygen that is not used in the electrolysis process can be recycled to the combustor (not shown) at biomass-fired power generator 12 to produce more carbon dioxide than is possible from air alone. This contributes to an overall increase in process efficiency.

In addition or in the alternative, oxygen can be part recycled to composting plant 18 (in particular where in-vessel composting is performed) to further add to the efficiency of the process.

The exhaust gas from biomass combustion may also have some oxygen which is 95%-98% removed in the exhaust gas processing step discussed below.

Power efficiency can be increased from about 35% if the exhaust gases exit power generator 12 at a temperature of about 450°-800° C. and are directed into a second, low temperature power plant 20. Power is generated at power plant 20 through use of a steam generator (not shown). Those skilled in the art will appreciate that power efficiency gains of around 15%-25% are possible through this effective re-use of exhaust gas, which obviates the need to burn additional biomass.

The waste heat from second power plant 20 is also very useable in the production of pelletised fertiliser product at composting plant 18.

The basic equations for producing urea and ammonium carbamate are as follows:

(1) Ammonia Production

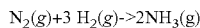

(2) Carbamate Production

(3) Urea Production

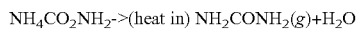

$NH_4CO_2NH_2$ liquid is ammonium carbamate and is a major component of the preferred liquor for practising the present invention (i.e. being a liquid mix of ammonium carbamate, urea, ammonia and water).

Carbon Dioxide Production

The process for cleaning the exhaust gas from biofuel combustion is as follows.

(a) biomass+air->Heat out plus exhaust gas (principally $CO_2$, $N_2$, some $O_2$) and other oxides of nitrogen.

The exhaust gas has around 10% to 20% carbon dioxide plus some $O_2$ and around 80% nitrogen.

The carbon dioxide is adsorbed and concentrated by reacting the exhaust gas with sodium carbonate as follows:

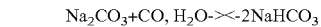

The reaction is forced to the right by increasing the partial pressure of the exhaust gas containing carbon dioxide and thus concentrating it to over 99% carbon dioxide.

The sodium bicarbonate solution is boiled and the carbon dioxide emerges $2NaHCO_3$->$NaCO_3+CO_2+H_2O$ Nitrogen Production The key principles in its production are outlined below.

(1) Exhaust gas->KOH scrubbed to remove any residual carbon dioxide.

(2) Compress residual exhaust gas to 200 atmospheres in four stages and cool with cooling water, and by ammonia refrigeration to approximately −30° C. (any moisture is hence solid water and is removed).

(3) The gas coming from the four compression stage is at 170° C. and is water cooled to approximately 10° C. to 30° C., and usually further cooled to approximately −30° C. by ammonia refrigeration.

(4) The step (3) product goes into a combined gas liquefier and bubble cap column separator. This separates out, via liquid separation, any surplus oxygen and the remaining gas is 98% $N_2$ or better and around 2% $0_2$, or less, as $N_2$ boils at −195.8° C. and $O_2$ at −183° C.

Hydrogen

According to the invention, the manufacture of hydrogen may also be by the water gas, or steam iron method or the electrolysis of water.

For example, water gas method is:

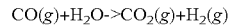

The electrolytic method is H, from water:

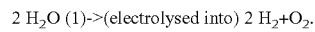

The electrolytic method is preferred.

A typical commercial electrolytic cell (not shown) produces the $H_2$ and $O_2$ separately in an approximately 15% sodium hydroxide solution (NaOH) at a temperature of 60° C. to 70° C. The $H_2$ is about 99.7% pure.

Around 1000 amperes are required to produce 0.0830 lbs of $H_2$, equivalent to 37.65 grams.

This means that 2.2 kWh produces 0.083 lb $H_2$ (37.65g) at a voltage of 2.2 volts/cell.

Hence one MW power per year produces about 150 tonnes per year of hydrogen.

If the electrolytic cell can have its temperature increased, then the power required for producing hydrogen and oxygen from water correspondingly decreases. Such temperature-increasing means can be provided by the waste heat 16 from power generator 12. In turn, this enables the minimum practical consumption of power for the production of hydrogen and oxygen in the electrolysis reaction.

The oxygen produced is principally recycled into the air going to the power generator 16 to burn biomass for electricity production. This enriches the $CO_2$ in the exhaust gas and thus is of benefit to the overall fertiliser and power generation process as more $CO_2$ is produced.

Additional increases in power generation efficiency can be achieved if waste gases are recycled back into power generator 16 along with the recycled oxygen from the electrolysis reaction. This process effect is explained by the fact that waste gases typically contain only low amounts of oxygen, but exit power generator 12 at a high temperature of around 400° C. to 800° C. Although more biomass is burned by the oxygen-augmented waste gases, the high temperature means that the amount of biomass required per megawatt hour is much reduced.

Urea vs Hydrogen Production

As an example, to produce 3000 tonnes of dry urea (($NH_2$)CO($NH_2$)), around 200 tonnes of hydrogen are required. Around 1600 tonnes of ammonia is produced by reacting nitrogen with hydrogen (i.e. $N_2+3H_2->2NH_3$) from this amount of hydrogen. The molecular weight of urea is 60 with the CO being about 28/60 (i.e. 47%) by weight. Hence 1600 tonnes of ammonia is equivalent to 3000 tonnes of urea. Hence 6000 tonnes of urea is equivalent to 3200 tonnes of ammonia and 2800 tonnes of nitrogen.

However, the preferred product for practising the present invention is ammonium carbamate liquor, being a combination of $NH_4CO_2NH_2$, urea, ammonia and water.

To make 100,000 tonnes of finished compost, about 50% of this initial carbon is lost to $CO_2$ in the composting process. Hence about 150,000 tonnes of wheat straw is required, which contains about 47% carbon (i.e. 70,500 tonnes of carbon) and thus needs about 2400 tonnes of N or 5200 tonnes or less of ammonium carbamate liquor as described above, owing to the fact that the liquor has a higher percentage of nitrogen and is already in the product in liquid form.

The Manufacture of Ammonia

As known to those skilled in the art, there are numerous processes for manufacturing ammonia, but the Nitrogen Engineering Corp process is suitable to practice the present invention. This uses a temperature of 500° C. and pressure of 200-300 atmospheres with a doubly promoted iron catalyst for a 20%-22% conversion to ammonia.

The residual gas is recirculated. It can use hydrogen from electrolytic cells. The reaction is highly exothermic so that the design of the converter controls the temperature for the 20-22% conversion.

The key reaction is:

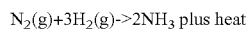

$N_2(g)+3H_2(g)->2NH_3$ plus heat

The waste gases pass through a waste heat boiler and can be used to generate steam for power generation.

Production of Phosphorous Products

Superphosphate is made by reacting rock phosphate with sulphuric acid and water, the relevant formula being:

$2[(CaF)Ca_4(PO_4)_3]+7H2SO_4+3H_2O->3CaH_4(PO_4)$
$2H_2O+2HF+7CaSO_4$

A higher quality product is double or triple superphosphate:

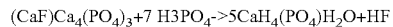

$(CaF)Ca_4(PO_4)_3+7 H3PO_4->5CaH_4(PO_4)H_2O+HF$

The waste heat from making sulphuric acid can be used to make steam and power.

Ammoniated Superphosphate

Superphosphate or double or triple superphosphate can be ammoniated to produce a fertiliser with desirable properties of chemical stability, uniformity of texture and resistance to moisture. Too much ammonia causes superphosphate to revert to insoluble forms.

Hence one of the preferred outcomes is the combination of super, double or triple-superphosphate with liquor made up of the following composition:

Urea 32.07% (i.e. ($NH_2$)CO($NH_2$)
$NH_3$ 28.9%
Ammonium Carbamate 18.1% (i.e. ($NH_4$)$CO_2$($NH_2$))
$H_2O$ 20.5%.

The ammoniation is produced simply by spraying a measured weight or volume of the above ammonium solution into a weighed quantity of solid material (super-, double- or triple superphosphate) and mixing in a 1-2 tonne rotary batch mixer. The mixture is discharged from the mixer, the discharged material feels moist and warm, but on cooling becomes dry and friable and cures rapidly and can be powderised prior to pelletising.

The ability to make a variety of inorganic fertilisers through practising the present invention, along with waste gas, some water and some onsite power, plus some purchased superphosphate (such as double or triple superphosphate) together with potassium from the power station biomass ash gives the capacity to produce inorganic fertiliser which is about 70% green or more (i.e. no carbon footprint) plus organic material (100% green) which is finally buried in a pellet form to yield a negative carbon footprint.

The optimum production of humic acid allows about 50% or more (possibly 75%) of the traditional P in DAP or MAP to be saved. This has widespread implications for preserving soil quality and in improving fertiliser efficiency.

More importantly, the present invention yields improved capacity to better optimise the slow and fast release of N, P and K, as described in Applicant's Patent Application WO 2007131301, than is possible by inorganic fertilisers alone. The on-site flexibility achieved allows much greater optimisation of the pelletised organic/inorganic fertiliser than just relying on purchased DAP and/or MAP and/or superphosphates in combination with Applicant's process and pelletised carbon nutrients from biomass.

The ability to make urea ammonia liquor via waste gases means that very large scale composting of biomass such as wheat and other grain straws can generally be guaranteed anywhere because of the availability of zero carbon-footprint nitrogen, and particularly in areas with little green waste or cattle or pig waste. The ability to produce a high quality compost with the correct amount of nitrogen means that the organic/inorganic pelletised fertiliser product quality can be very efficiently made and this in turn gives much added capability and certainty to farmers.

The ability to also make ammoniated superphosphate using the same liquor comprising urea, ammonia, ammonium carbamate and water, produced from the same waste gases in its production also means that 70% or more of the organic/inorganic fertiliser is 'green'.

The integrated fertiliser process using power plant waste gases has an improved capacity to optimise the C (humus), N, P, K and trace elements that plants require for optimum growth in particular areas of land, varying rainfall patterns and the optimum slow and fast release of C (humus), N, P, K for optimum plant growth.

Integrated systems and methods of the present invention have the following beneficial effects:

1. Maximising the composting and processing of high carbon fibrous materials into 'humic composts' via access to a very predictable on-site source and low cost source of nitrogen that is independent of other green waste sources (not combined with P) and does not use natural gas (which creates additional polluting greenhouse gases).

2. Producing an organic fertilizer product which can have up to 50% more than the carbon/humus content compared to a recycled green waste product alone. For example, a long term composted 100% wheat straw product may have a carbon content of 39% plus (dry basis) versus a long term green waste carbon content of say 15%. Mixtures of straw, green waste and recycled compost produce the best results. If both finished products have a finished C:N ratio of, approximately 15:1 (assuming that the process starts at C:N ratio of 30 and reduces over time), then the amount of humic C and N in the wheat straw compost (depending on time) may be significantly higher that of the green waste product (on a dry basis).

3. Maximising the amount of humic acid in compost has a significant technical import in that the efficiency of the plant to use the phosphorous 'P' significantly improves and field and pot trials have shown that a reduction of at least 50% and possibly 75% of the P and DAP and MAP inorganic fertilisers can be achieved.

4. Maximising flexibility in optimising the humic C, N, P, K of the finished pelletised organic/inorganic fertilizer with a very small to zero and preferably a positive green environmental impact. A green fertilizer product with a 24% plus 'C' nutrient content has 150% of the greenhouse credit potential of one with a 15% humic 'C' content when this carbon is buried in the ground. The 24% plus 'C' nutrients (dry basis) in large quantities from many organic wastes cannot be made without access to a large zero environmental impact process designed to deliver additional large scale flexible, predictable sources of 'N' for fertiliser production. The burying of green 'N' also has a beneficial environmental impact as against 'N' in DAP and MAP made from natural gas.

The word 'comprising' and forms of the word 'comprising' as used in this description and in the claims do not limit the invention claimed to exclude any variants or additions. Modifications and improvements to the invention will be readily apparent to those skilled in the art. Such modifications and improvements are intended to be within the scope of this invention.

The claims defining the invention are as follows:

1. A method for producing electric power and fertiliser, the method comprising the steps of:
    combusting biomass to produce energy for the generation of electric power and an exhaust gas;
    producing a liquor from compounds extracted from the exhaust gas; and
    producing a fertiliser by composting organic materials in the presence of the liquor.

2. A method according to claim 1, wherein the liquor includes one or more nitrogenous compounds in liquid phase.

3. A method according to claim 2, wherein the nitrogeneous compounds include ammonia, ammonium carbamate and urea.

4. A method according to claim 1, wherein the liquor includes water.

5. A method according to claim 1, wherein the organic materials include the straw of cereal crops.

6. A method according to claim 1, wherein humic carbon comprises approximately 26% to 40% of the fertiliser on a dry-weight basis.

7. A method according to claim 1, wherein the step of producing a liquor includes:
    extracting carbon dioxide and nitrogen from the exhaust gas;
    obtaining a source of hydrogen; and
    producing urea and ammonium carbamate in liquid phase from the carbon dioxide, nitrogen and hydrogen.

8. A method according to claim 7, wherein the step of obtaining a source of hydrogen includes utilising the electric power to electrolyse water and thereby generate hydrogen and oxygen.

9. A method according to claim 8, further including a step of utilising the oxygen in the step of composting the organic materials in the presence of the liquor.

10. A method according to claim 1, wherein the combusting step includes pyrolysing the biomass to produce a char.

11. A method according to claim 10, further including the step of reacting the char with water to produce carbon monoxide and hydrogen.

12. A method according to claim 7, wherein the step of obtaining a source of hydrogen includes pyrolysing the biomass to produce a char and utilising hydrogen produced by reacting the char with water.

13. A method according to claim 1, further including the steps of:
    producing inorganic fertiliser components from compounds extracted from the exhaust gas; and
    producing a combined fertiliser comprising organic and inorganic constituents by combining the inorganic fertiliser components with the fertiliser produced by composting the organic materials in the presence of the liquor.

14. A method according to claim 13, wherein the inorganic fertiliser components include members selected from the group consisting of ammonia, ammoniated liquor, DAP, MAP and triple superphosphate.

15. A method according to claim 13, wherein the inorganic fertiliser components are produced in powdered form and the step of producing a combined fertiliser includes producing pellets comprising powdered inorganic fertiliser components and fertiliser produced by composting the organic materials in the presence of the liquor.

16. An integrated system for producing electric power and fertiliser, the system comprising:
    a biomass combustion facility for combusting biomass to produce energy for electric power and an exhaust gas; and
    a composting facility for producing compost from organic materials,
    wherein a liquor is produced from compounds extracted from the exhaust gas and directed into the composting facility to produce a fertiliser by composting organic materials in the presence of the liquor.

17. A system according to claim 16, wherein the liquor includes one or more nitrogenous compounds in liquid phase.

18. A system according to claim 16 wherein the nitrogeneous compounds include ammonia, ammonium carbamate and urea.

19. A system according to claim 16, wherein the liquor includes water.

20. A system according to claim 16, wherein the organic materials include the straw of cereal crops.

21. A system according to claim 16, wherein humic carbon comprises approximately 26% to 40% of the fertiliser on a dry-weight basis.

22. A system according to claim 16, wherein the liquor is produced by:
    extracting carbon dioxide and nitrogen from the exhaust gas;
    obtaining a source of hydrogen; and
    producing urea and ammonium carbamate in liquid phase from the carbon dioxide, nitrogen and hydrogen.

23. A system according to claim 22, wherein the source of hydrogen is the water-gas method or from the electrolysis of water, said electrolysis being performed by utilising the electric power from the biomass combustion facility to generate hydrogen and oxygen.

24. A system according to claim 23, wherein organic materials are composted in the presence of oxygen and the liquor, said oxygen being sourced from the electrolysis of water.

25. A system according to claim 16, wherein the biomass is pyrolysed to produce a char.

26. A system according to claim 25, wherein the char is reacted with water to produce carbon monoxide and hydrogen.

27. A system according to claim 22, wherein the source of hydrogen is hydrogen produced from reacting char with water, the char obtained by pyrolysing the biomass.

28. A system according to claim 16, wherein:
   inorganic fertiliser components are produced from compounds extracted from the exhaust gas; and
   a combined fertiliser comprising organic and inorganic constituents is produced by combining the inorganic fertiliser components with the fertiliser produced by composting the organic materials in the presence of the liquor.

29. A system according to claim 28, wherein the inorganic fertiliser components include members selected from the group consisting of ammonia, ammoniated liquor, DAP, MAP and triple superphosphate.

30. A system according to claim 28, wherein the inorganic fertiliser components are produced in powdered form and the combined fertiliser is produced by producing pellets of powered inorganic fertiliser components and fertiliser produced by composting the organic materials in the presence of the liquor.

* * * * *